US011160566B2

(12) United States Patent
Birkbeck et al.

(10) Patent No.: US 11,160,566 B2
(45) Date of Patent: Nov. 2, 2021

(54) SURGICAL ROTATIONAL CUTTING TOOL AND METHOD

(71) Applicant: DEPUY IRELAND UNLIMITED COMPANY, County Cork (IE)

(72) Inventors: Alec Birkbeck, Leeds (GB); Graeme Dutton, Burnley (GB); David Horne, Leeds (GB); Thomas Maack, Lebrade (DE); Richard Patnelli, Leeds (GB)

(73) Assignee: DEPUY IRELAND UNLIMITED COMPANY

( * ) Notice: Subject to any disclaimer, the term of this patent is extended or adjusted under 35 U.S.C. 154(b) by 175 days.

(21) Appl. No.: 16/485,494

(22) PCT Filed: Jan. 24, 2018

(86) PCT No.: PCT/EP2018/051682
§ 371 (c)(1),
(2) Date: Aug. 13, 2019

(87) PCT Pub. No.: WO2018/149602
PCT Pub. Date: Aug. 23, 2018

(65) Prior Publication Data
US 2020/0046378 A1 Feb. 13, 2020

(30) Foreign Application Priority Data
Feb. 14, 2017 (GB) ..................................... 1702404

(51) Int. Cl.
*A61B 17/16* (2006.01)

(52) U.S. Cl.
CPC ...... *A61B 17/1668* (2013.01); *A61B 17/1615* (2013.01)

(58) Field of Classification Search
CPC .. A61L 17/16; A61L 17/1613; A61L 17/1615; A61L 17/1617; A61L 17/164;
(Continued)

(56) References Cited

U.S. PATENT DOCUMENTS 6,258,093 B1 * 7/2001 Edwards ............... A61B 17/164
606/80
8,029,509 B2 * 10/2011 Ducharme ......... A61B 17/1615
606/80
(Continued)

FOREIGN PATENT DOCUMENTS

DE 19850980 A1 5/2000
WO WO 2004014241 A1 2/2004
(Continued)

*Primary Examiner* — Eric S Gibson (57) ABSTRACT

A surgical rotational cutting tool, a surgical kit and a method of preparing a femur to receive a stem of a femoral prosthetic. The tool includes a longitudinal axis and a shaft extending along the longitudinal axis, which has a proximal end and a distal end. The tool also includes a head located at the distal end of the shaft. The head includes a pointed distal tip, a bone contacting outer surface having a portion which curves inwards toward the longitudinal axis as it approaches the tip, and a plurality of flutes. The edges of distal parts of neighboring pairs of the flutes meet to define a plurality of cutting edges which extend proximally from the pointed distal tip. A proximal part of each flute extends proximally across the curved portion.

16 Claims, 7 Drawing Sheets

(58) Field of Classification Search
CPC .............. A61L 17/1662; A61L 17/1664; A61L 17/1668
See application file for complete search history.

(56) References Cited

U.S. PATENT DOCUMENTS

| | | | | |
|---|---|---|---|---|
| 8,460,298 | B2* | 6/2013 | O'Donoghue | A61B 17/1615 606/80 |
| 8,852,222 | B2* | 10/2014 | O'Sullivan | A61B 17/32002 606/180 |
| 9,179,923 | B2* | 11/2015 | Gubellini | B23C 5/1009 |
| 9,526,508 | B2* | 12/2016 | Burke | A61B 17/1615 |
| 9,883,873 | B2* | 2/2018 | Kulas | A61B 17/1695 |
| 9,924,952 | B2* | 3/2018 | Kulas | A61B 17/1615 |
| 9,955,981 | B2* | 5/2018 | Kulas | A61B 17/1695 |
| 10,105,147 | B2* | 10/2018 | Burke | B23C 5/10 |
| 10,335,166 | B2* | 7/2019 | Kulas | B23C 5/1009 |
| 10,507,028 | B2* | 12/2019 | Kulas | A61B 17/1615 |
| 10,912,572 | B2* | 2/2021 | Kunz | A61C 8/0089 |
| 2006/0127847 | A1 | 6/2006 | Danger | |
| 2007/0213736 | A1* | 9/2007 | Ducharme | A61B 17/1615 606/80 |
| 2008/0132929 | A1* | 6/2008 | O'Sullivan | A61B 17/32002 606/170 |
| 2008/0140078 | A1* | 6/2008 | Nelson | A61B 17/1615 606/80 |
| 2009/0048602 | A1 | 2/2009 | O'Donoghue | |
| 2011/0238099 | A1 | 9/2011 | Loreth | |
| 2011/0319895 | A1 | 12/2011 | Gamache | |
| 2012/0150209 | A1* | 6/2012 | Gubellini | B23C 5/1009 606/170 |
| 2013/0274779 | A1* | 10/2013 | Kulas | A61B 17/1615 606/180 |
| 2014/0186797 | A1* | 7/2014 | Haus | A61C 8/0001 433/173 |
| 2014/0309641 | A1* | 10/2014 | Bourque | A61B 17/16 606/80 |
| 2015/0025559 | A1 | 1/2015 | Kulas | |
| 2015/0127005 | A1* | 5/2015 | Mcmanus | A61B 17/1684 606/80 |
| 2015/0150565 | A1* | 6/2015 | Huwais | A61B 17/1615 606/84 |
| 2015/0173776 | A1* | 6/2015 | Burke | A61B 17/162 606/80 |
| 2015/0342617 | A1* | 12/2015 | Kunz | A61C 1/14 433/75 |
| 2016/0106441 | A1 | 4/2016 | Teisen | |
| 2020/0046378 | A1* | 2/2020 | Birkbeck | A61B 17/1615 |

FOREIGN PATENT DOCUMENTS

| | | |
|---|---|---|
| WO | WO 2007010389 A1 | 1/2007 |
| WO | WO 2011023381 A1 | 3/2011 |
| WO | WO 2014143597 A1 | 9/2014 |
| WO | WO 2016160385 A1 | 10/2016 |

* cited by examiner

SURGICAL ROTATIONAL CUTTING TOOL AND METHOD

CROSS REFERENCE TO RELATED PCT APPLICATION

This application is a National Stage 35 U.S.C. 371 of International Patent Application PCT/EP2018/051682 filed Jan. 24, 2018, which claims priority to United Kingdom Application No. GB1702404.3, filed Feb. 14, 2017.

FIELD OF THE INVENTION

This invention relates to a surgical rotational cutting tool. The invention also relates to a surgical kit comprising at least one surgical rotational cutting tool. This invention further relates to a method of preparing a femur to receive a stem of a femoral prosthetic.

BACKGROUND OF THE INVENTION

Hip replacement is a surgical procedure in which the hip joint is replaced by a prosthetic implant. As part of the hip replacement procedure, the femoral head is replaced with a femoral prosthetic that includes a stem, which is inserted into the medullary canal at a proximal end of the femur. The femoral prosthetic also includes a bearing surface, which is received within the acetabulum of the patient. The procedure may in some cases also involve inserting an acetabular cup into the acetabulum of the patient, for receiving the bearing surface of the femoral prosthetic.

To prepare the femur to receive the femoral prosthetic, a cut is made at the proximal end of the femur, to remove the femoral neck and head. Thereafter tools such as drills and reamers are used to first gain access to the medullary canal and then to remove bone from the surface of the canal so as to shape it to receive the stem of the femoral prosthetic.

More particularly, a surgical rotational cutting tool having a sharp tip may first be used to drill into the proximal cut surface of the femur to gain access to the canal. Thereafter, a tool such as an elongate reamer, which typically includes cutting edges located along its side surfaces, may then be used to remove bone from the sidewalls of the medullary canal until it is appropriately shaped to receive the stem. This step may include removing bone from the sides of the entrance to the medullary canal, to widen it. This step may also include removing a part of the greater trochanter that may remain at the proximal end of the femur following the cutting away of the femoral neck and head.

DE 19850980 A1 describes a reamer that has two straight, double-edged, longitudinally adjacent bits with longitudinal axis sloping towards each other. A number of blades run parallel with the longitudinal axes. The peripheral surface between the two blades is concave. The blades extend of the entire proximal part and over the adjacent part of the distal part.

US 2006/127847 A1 describes a rotating instrument made of a ceramic material and comprising a shaft and a working member which is secured to the shaft or can detachably be secured thereto, wherein at least part of the working member is made from a ceramic material.

US 2011/319895 A1 describes an awl that provides for creating an accurate hole in a bone, such as for implantation of a suture anchor. The awl comprises an elongated shaft having a distal tip which terminates in a sharp point adapted to penetrate bone. At least one cutting flute is provided on the shaft and has a longitudinally extending cutting edge formed on the shaft proximal to and adjacent to the sharp point whereby to allow removal of bone via the cutting flute upon rotation of the shaft about a central longitudinal axis thereof inside of the bone.

US 2016/106441 A1 describes a bone access instrument comprising a shaft having a first shaft portion and a second shaft portion. The first shaft portion has a first diameter, a proximal end, a tapered distal end including at least three straight cutting edges being equally spaced circumferentially about the tapered distal end, and at least three flutes extending from the tapered distal end toward the proximal end in a parallel relationship to one another. The second shaft portion has a second diameter and a tapered distal end. The second diameter is less than the first diameter, and the second shaft portion extends axially from the distal end of the first shaft portion.

US 2015/025559 A1 describes a surgical bur that includes a body and a drill point. The body includes flutes and lands. Each of the flutes includes a cutting edge, a rake face, and a clearance surface. Each of the lands is convex-shaped and disposed between a pair of the flutes. The drill point includes axial relief surfaces. Each of the axial relief surfaces has a planar area, is distinct from the lands and borders (i) a distal portion of one of the cutting edges, (ii) one of the lands, and (iii) one of the clearance surfaces.

US 2008/132929 A1 describes a surgical bur including a shaft with a bur head. A number of flutes are formed on the bur head. Each flute has a cutting edge. The flutes are formed so that some of the flutes having cutting edges emerge from the bur head at locations relatively close to the distal end tip of the head. Still other flutes are formed so as to have cutting edges that start, extend proximally rearward, from locations that are, spaced proximal from the distal end tip.

WO 2007/010389 A1 describes a surgical bur including a shaft with a bur head. A number of flutes are foil led on the bur head. Each flute has a cutting edge. The flutes are formed so to have cutting edges extend variable lengths along the outer surface of the bur head.

WO 2014/143597 A1 describes a retro guidewire reamer includes a cutting member, and a mechanism for moving the cutting member from a closed position to a deployed position in a single manual motion. Once a desired size of a bone tunnel is established, a surgeon uses the reamer to create a primary bone tunnel over a guidewire from the outside in. The surgeon retracts the guidewire, and activates the mechanism to deploy the cutting member within the bone joint to conform to the size of a tendon graft. The surgeon uses the deployed cutting member to create a counter bore through the bone in a retrograde manner. Once the counter bore is drilled, the surgeon activates the mechanism to close the cutting member, allowing the reamer to be withdrawn through the primary tunnel. The retro guidewire reamer can be used to provide more accurate bone tunnel placement during ligament reconstruction surgery WO 2004/014241 A1 describes a drill bit comprising: a shaft which has a pyramidal shaped end defining a drill tip with a plurality of edges defining the pyramidal shape; and one or more recesses for directing away debris produced whilst drilling, the or each recess having a first portion extending along the shaft and a second portion which extends along the drill tip, wherein the second portion of the or each recess extends along an edge of the drill tip.

SUMMARY OF THE INVENTION

Aspects of the invention are set out in the accompanying independent and dependent claims. Combinations of features from the dependent claims may be combined with features of the independent claims as appropriate and not merely as explicitly set out in the claims.

According to an aspect of the invention, there is provided a surgical rotational cutting tool comprising:
- a longitudinal axis;
- a shaft extending along the longitudinal axis and having a proximal end and a distal end; and
- a head located at the distal end of the shaft, the head comprising:
  - a pointed distal tip;
  - a bone contacting outer surface having a curved portion which curves inwards toward the longitudinal axis as it approaches the tip; and
  - a plurality of flutes positioned circumferentially around the head, wherein each flute includes a proximal part and a distal part, wherein each distal part extends proximally from the pointed distal tip, wherein the edges of the distal parts of neighbouring pairs of said circumferentially positioned flutes meet to define a plurality of cutting edges which extend proximally from the pointed distal tip, and wherein the proximal part of each flute extends proximally across the curved portion of the bone contacting outer surface.

The pointed distal tip and cutting edges, which extend proximally therefrom, can be used to cut or drill directly into bone. The inwardly curving bone contacting outer surface, across which the proximal part of each flute extends can act to inhibit the lateral removal of bone by the head when the tool is moved laterally within the bone. This can allow a surgeon to use the tool more safely and precisely, particularly in situations where he or she wants to avoid any lateral drilling/cutting of the bone by the head of the tool when it is inside the bone. In particular, because the proximal parts of each flute extend proximally across the curved portion of the bone contacting outer surface, the edges of these parts of the flutes may be relatively shallow, particularly compared to the sharper cutting edges formed by the edges of distal parts of the flutes, whereby they would are unable to cut laterally into a surface of the bone. Also, the curve of the bone contacting outer surface presents a rounded surface at the sides of the head, which may inhibit the lateral removal of bone by the head even when the lateral movement within the bone involves rotation of the head within a plane containing the longitudinal axis of the tool.

In some examples, a plurality of further cutting edges may be located on the shaft intermediate the head and the proximal end of the shaft. These further cutting edges may be used to make lateral cuts into the bone at a position located proximally with respect to the head. These cuts can be made by moving the tool laterally within the bone, so as to urge the further cutting edges laterally against the surface of the bone. Because the head, as discussed above, has features which prevent lateral drilling/cutting by the head when it is inside the bone, the lateral removal of bone by the further cutting edges located on the shaft can be performed in a controlled manner. In particular, the surgeon need not worry about the lateral movements of the tool for urging the further cutting edges against the bone causing any unwanted removal of bone by the head. Moreover, it is envisaged that the surgeon may use the head as a non-cutting pivot point to leverage the plurality of further cutting edges located on the shaft against the surface of the bone.

Thus, embodiments of this invention can allow the functions of a pointed tip for initially cutting or drilling into a bone, and a lateral reamer, to be combined in a single surgical rotational cutting tool. This can save manufacturing costs in the production surgical instruments for performing a surgical procedure, and can reduce the weight and size of a surgical kit incorporating the tool.

One example of the use of a tool according to an embodiment of this invention may be during a hip replacement procedure, for preparing a femur to receive a stem of a femoral prosthetic. In particular, the pointed distal tip and cutting edges, which extend proximally from the tip, can be used to cut or drill into the proximal cut surface of a femur to gain access to the medullary canal. Thereafter, with the head of the tool located inside the medullary canal, the further cutting edges noted above may be used to remove bone from the sidewalls of the medullary canal until it is appropriately shaped to receive broaches and then the stem. This may include removing bone from the sides of the entrance to the medullary canal, to widen it, and/or removing a part of the greater trochanter that may remain at the proximal end of the femur following the cutting away of the femoral neck and head.

In some embodiments, the angle(s) at which the edges of the distal parts of said neighbouring pairs of flutes meet to define the plurality of cutting edges are more acute than the angle(s) at the edges formed between the proximal part of each flute and the bone contacting outer surface. As noted above, the relative shallowness of the edges formed between the proximal part of each flute and the bone contacting outer surface can prevent them from cutting laterally into a surface of the bone.

The cutting edges extending proximally from the pointed distal tip may be concave. Each flute may have a concave surface. The concave surface may be a concave cylindrical surface. This can conveniently allow the head of the tool to be formed using a cylindrical milling cutter or ball nose cutter, for forming the flutes and the pointed distal tip. Other cross sectional shapes for the flutes (e.g. V-shaped, or square-shaped) are envisaged. Where the cross sectional shape of the flutes is e.g. V-shaped, or square-shaped, an end mill cutter may be used to form them instead. An axis (e.g. a cylindrical axis) of the concave (e.g. cylindrical) surface of each flute may be oriented at an angle in the range $20° \leq \theta \leq 80°$ with respect to the longitudinal axis. This may be implemented by appropriate orientation of a cylindrical milling cutter or appropriate movement of a ball nose cutter during manufacture. The path of each flute as it extends proximally from the distal tip may be substantially straight, although it is also envisaged that the path may be curved. It is also envisaged that each flute may be tilted or angled in one direction to create edges with different angles at either side of the groove formed by each flute. This may allow the cutting edges of each flute to have a preferential rotation cutting direction compared to the opposite rotational direction. Moreover, the groove shape or tilt may change across the surface of the head, to further vary the edge angle.

The proximal parts of respective neighbouring pairs of flutes may be separated from each other by a respective part of the curved portion of the bone contacting outer surface. Each respective part of the curved portion of the bone contacting outer surface may be substantially V-shaped. The apex of each substantially V-shaped part may meet a proximal end of the cutting edge that is defined by the respective neighbouring pair of flutes. Because the apex of the V-shaped part is located on the portion of the bone contacting outer surface that curves inwards toward the longitudinal axis as it approaches the tip, the point formed by the apex of the substantially V-shaped part and the proximal end of the cutting edge that is defined by the respective neighbouring pair of flutes is less sharp than it would otherwise be. This can prevent the apex from cutting laterally into a bone in contact with the bone contacting outer surface.

The bone contacting outer surface may have a proximal portion that curves inwards toward the longitudinal axis with increasing distance from the pointed distal tip, to form a neck of the tool. The proximal part of each flute may extend proximally across the proximal portion of the bone contacting outer surface. This arrangement can allow the flutes to dispense bone that has been cut away by the cutting edges of the head to be dispensed proximally, to the rear of the head.

At least part of the bone contacting outer surface may be substantially spherical. It is envisaged that this may be the optimal shape for inhibiting the lateral removal of bone by the head even when lateral movement of the tool within the bone involves rotation of the head within a plane containing the longitudinal axis of the tool, as discussed above.

The flutes are equally circumferentially spaced around the head. The tool may have exactly four flutes.

The surgical rotation cutting tool may be implemented as, or in, a number of different kinds of surgical instrument. By way of example only, it is envisaged that the surgical rotation cutting tool may be a surgical drill bit, a rotary initiator device (also known as a canal initiator tip), or a straight reamer.

According to another aspect of the invention, there is provided a surgical kit comprising a plurality of surgical rotational cutting tools of the kind set out above. At least one of the surgical rotational cutting tools may be of a different size to at least one other of the surgical rotational cutting tools. The kit may, for instance be for a hip replacement procedure.

According to a further aspect of the invention, there is provided a method of preparing a femur to receive a stem of a femoral prosthetic, the method comprising:

cutting away the head and neck of the femur; and using a surgical rotational cutting tool of the kind set out above to cut into a proximal cut surface of the femur to gain access to the medullary canal.

As noted above, the tool may include a plurality of further cutting edges located on the shaft and proximally with respect to the head. In such examples, the method may also include positioning the tool so that the head is located inside the medullary canal while the further cutting edges are located at the entrance to the medullary canal. The method may further include moving the tool laterally to use the plurality of further cutting edges to remove bone to widen the entrance to the medullary canal.

The method may also include moving the tool laterally to use the plurality of further cutting edges to remove at least part of the greater trochanter.

BRIEF DESCRIPTION OF THE DRAWINGS

Embodiments of the present invention will be described hereinafter, by way of example only, with reference to the accompanying drawings in which like reference signs relate to like elements and in which.

DETAILED DESCRIPTION

Embodiments of the present invention are described in the following with reference to the accompanying drawings.

Embodiments of this invention can provide a surgical rotation cutting tool, a surgical kit including one or more such tools, and to a method for using such a tool in the preparation of a femur to receive a stem of a femoral prosthetic. The examples shown in the figures relate particularly to a surgical rotation cutting tool that comprises a surgical drill bit. However, it is envisaged that a surgical rotation cutting tool having features of the kind described herein may be implemented as, or in, a number of different kinds of surgical instrument. For instance, it is envisaged that a surgical rotation cutting tool may be implemented as a rotary initiator device (also known as a canal initiator tip), or a straight reamer.

Figure 1:
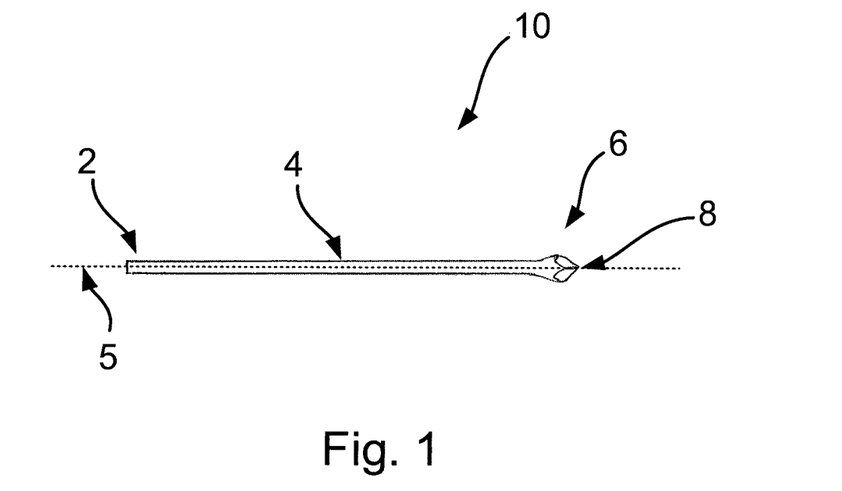
FIGS. 1 and 2 show two views of a surgical rotational cutting tool according to an embodiment of this invention.

FIG. 1 shows a side view of a surgical drill bit 10 for a bone drill according to an embodiment of this invention. An isometric view of the drill bit 10 is shown in FIG. 2.

Figure 2:
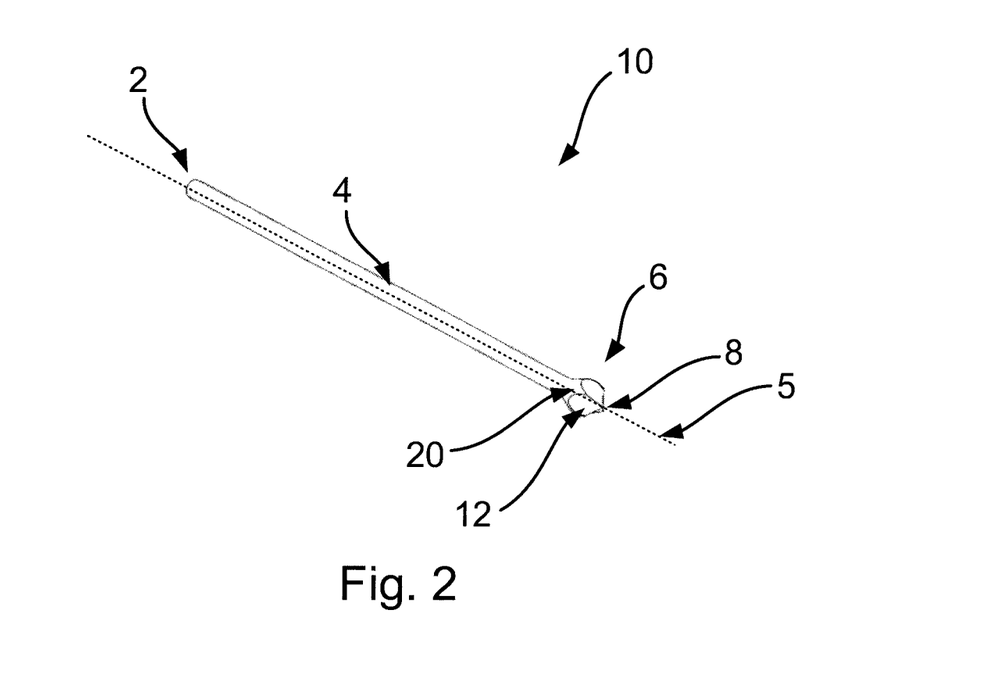

The drill bit 10 has a longitudinal axis, which is indicated in FIGS. 1 and 2 by the dotted line labelled 5. The drill bit 10 also has a shaft 4. The shaft 4 may be elongate. The shaft 4 extends along the longitudinal axis 5. The shaft has a proximal end 2. The proximal end may be attachable to a bone drill. The proximal end 2 may form a shank, as shown in FIGS. 1 and 2. To attach the drill bit 10 to the bone drill, the shank may be received in a chuck of the bone drill. The drill bit 10 also includes a distal end. As shown in the Figures, the drill bit 10 has a head 6, which is located at the distal end of the shaft 4. The head 6 may be used to drill into the surface of a bone, typically by pressing the head 6 against the bone, in a direction along the longitudinal axis 5.

Figure 3:
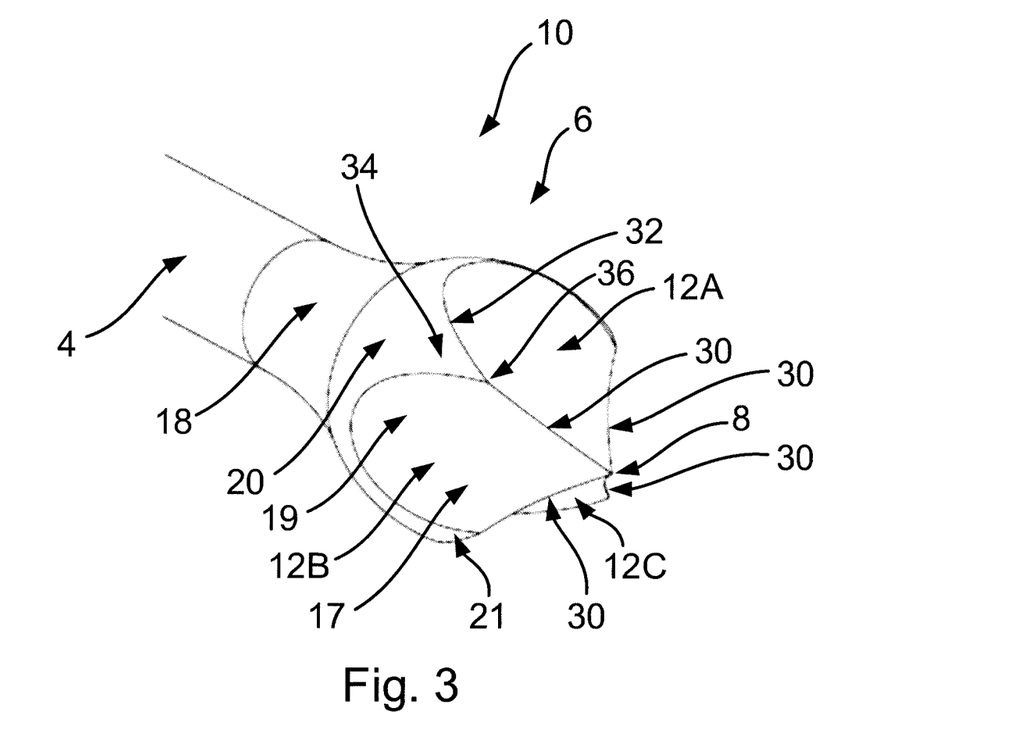
FIG. 3 shows a detailed view of the head of the tool of FIGS. 1 and 2.

FIG. 3 shows a detailed view of the head 6 of the drill bit 10.

The head 6 has a pointed distal tip 8. The pointed distal tip 8 is typically the first part of the drill bit 10 encounter the surface of a bone as the drill bit 10 drills into it. The pointed distal tip 8 may typically be sharp, so as to aid the entrance of the head 6 into the bone.

The head 6 also includes a plurality of flutes 12. In the present example, the head 6 includes four flutes 12A, 12B, 12C, 12D, although it is envisaged that a greater number or fewer number of flutes 12 may be provided. Each flute 12A, 12B, 12C, 12D is positioned circumferentially around the head 6. For instance, the flutes 12A, 12B, 12C, 12D may be evenly spaced around the circumference of the head 6.

Each flute 12A, 12B, 12C, 12D includes a distal part 17 and a proximal part 19. As can be seen best in FIG. 3, each distal part 17 of each flute 12A, 12B, 12C, 12D extends proximally from the pointed distal tip 8. As is also shown in FIG. 3, the edges of the distal parts 17 of neighbouring pairs of the flutes 12A, 12B, 12C, 12D meet to define a plurality of cutting edges 30. The cutting edges 30 each extend proximally from the pointed distal tip 8. For instance, in the present example, the edges of a first pair of flutes 12A, 12B meet to form a first cutting edge 30, the edges of a second pair of flutes 12B, 12C meet to form a second cutting edge 30, the edges of a third pair of flutes 12C, 12D meet to form a third cutting edge 30, and the edges of a fourth pair of flutes 12D, 12A meet to form a fourth cutting edge 30.

In the present example, the surface of each flute 12A, 12B, 12C, 12D has the shape of a partial cylinder (this is discussed in more detail below in relation to FIG. 4). The cylindrical shape of the surfaces of the flutes 12A, 12B, 12C, 12D gives rise to cutting edges which are concave, as is visible in FIG. 3. This curvature of the cutting edges 30 lead to a slightly sharper tip, owing the reduction in the angle of the cutting edge 30 relative to the longitudinal axis 5 at positions closer to the pointed distal tip 8.

In use, the cutting edges 30 rotate about the longitudinal axis 5, cutting into the bone as they do so. The flutes 12A, 12B, 12C, 12D generally act to dispense bone that has been cut away by the cutting edges 30 to the rear of the head 6, providing space for further bone to be removed.

The head 6 also includes a bone contacting outer surface 20. The bone contacting outer surface 20 has a curved portion 21, which curves inwards toward the longitudinal axis 5 as it approaches the pointed distal tip 8. The curvature of the curved portion 21 of the bone contacting outer surface 20, as viewed in a plane containing the longitudinal axis 5 may be substantially circular. The proximal part 19 of each flute 12A, 12B, 12C, 12D extends proximally across this curved portion 21 of the bone contacting outer surface 20, as can be seen in FIG. 3. The edges 32 between the proximal parts 19 of each flute 12A, 12B, 12C, 12D may be curved (e.g. substantially elliptical).

The inwardly curving portion 21 of the bone contacting outer surface 20, across which the proximal part 19 of each flute 12A, 12B, 12C, 12D extends can act to inhibit the lateral removal of bone by the head 6 when the drill bit 10 is moved laterally within the bone. This can allow a surgeon to use the drill bit 10 more safely and precisely, particularly in situations where he or she wants to avoid any lateral drilling/cutting of the bone by the head 6.

In particular, because the proximal parts 19 of each flute 12A, 12B, 12C, 12D extend proximally across the curved portion 21 of the bone contacting outer surface 20, the edges 32 of these parts 19 of the flutes 12A, 12B, 12C, 12D may be relatively shallow, particularly compared to the cutting edges 30. The edges 32 may therefore be unable to cut laterally into a surface of the bone as the drill bit rotates around the longitudinal axis 5. Also, the curve of the bone contacting outer surface 20 may present a rounded surface at the sides of the head 6, which may inhibit the lateral removal of bone by the head 6 even when the drill bit is rotated within a plane containing the longitudinal axis 5, as with be discussed below in relation to FIG. 6.

As can be seen in FIG. 3, in the present example, the proximal parts 19 of respective neighbouring pairs 12A, 12B; 12B, 12C; 12C, 12D; 12D, 12A of flutes 12 are separated from each other by a respective part 34 of the curved portion 21 of the bone contacting outer surface 20. Each respective part 34 of the curved portion 21 of the bone contacting outer surface 20 may be substantially V-shaped. The apex 36 of each substantially V-shaped part 34 may meet a proximal end of the cutting edge 30 that is defined by the edges of the distal parts 17 of the respective neighbouring pair 12A, 12B; 12B, 12C; 12C, 12D; 12D, 12A of flutes 12. Note that because the curved portion 21 of the bone contacting outer surface 20 curves inwards toward the longitudinal axis 5 as it approaches the pointed distal tip 8, the apex 36 is made less prominent at the lateral sides of the head 6 that it would otherwise be. This can significantly reduce the tendency of the head 6 to cut laterally into the bone as the drill bit is moved laterally, e.g. rotated within a plane containing the longitudinal axis 5.

In the present example, the bone contacting outer surface 20 also includes a proximal portion that curves inwards toward the longitudinal axis 5 with increasing distance from the pointed distal tip 8, thereby to form a neck 18 of the surgical drill bit 10. The neck 18 is located proximal the head 6. In such examples, the shaft 4 of the surgical drill bit 10 may be narrower than the head 6. This has the potential benefit of providing a space to the rear of the head 6 to receive bone material that is dispensed there by the flutes. In this respect, note that it is envisaged that the proximal part 19 of each flute 12A, 12B, 12C, 12D may extend proximally across the proximal portion of the bone contacting outer surface 20 as can be seen in FIG. 3. It is also envisaged that the relatively narrow shaft 4 may comprise a flexible portion, allowing the drill bit 10 to travel around one or more bends inside the bone.

Figure 4:
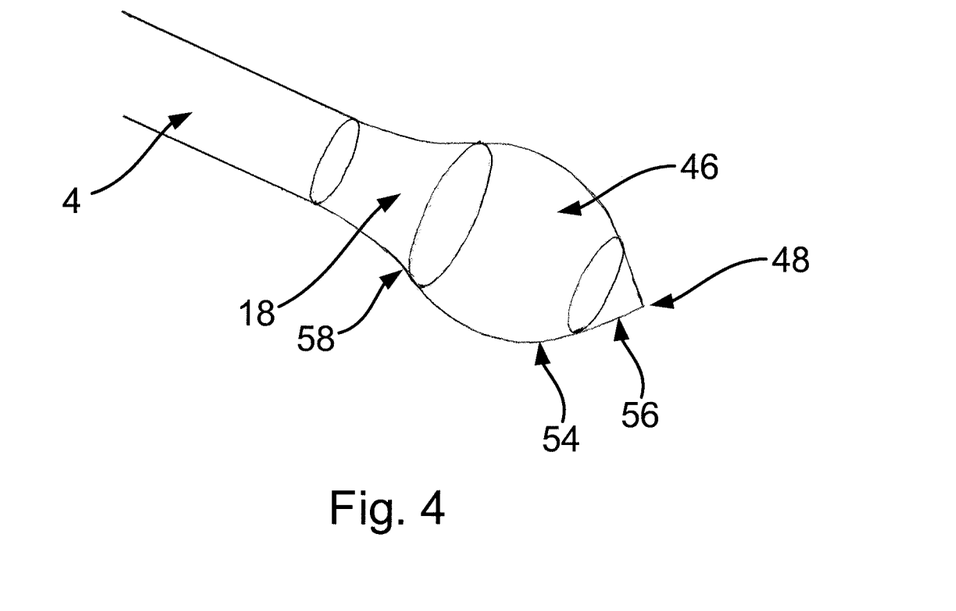
FIG. 4 illustrates a stage in the manufacturing of the surgical rotational cutting tool of FIGS. 1 to 3, prior to the formation of the flutes of the tool.

FIG. 4 illustrates a stage in the manufacturing of the surgical drill bit of FIGS. 1 to 3, prior to the formation of the flutes 12A, 12B, 12C, 12D. It is envisaged that the same or a similar approach may be used for manufacturing other surgical rotational cutting tools such as rotary initiator devices (also known as a canal initiator tips), or straight reamers.

To form the drill bit 10, there may first be provided a work piece that comprises the shaft 4 of the drill bit 10, with a head portion 46. In the present example, the head portion has a curved outer surface, the remaining parts of which (i.e. following the formation of the flutes 12A, 12B, 12C, 12D) will subsequently form the bone contacting outer surface 20 of the drill bit. A first part 54 of the curved outer surface may be substantially spherical. Following the formation of the flutes 12A, 12B, 12C, 12D, remaining parts of a distal part of the first part 54 of the curved outer surface may subsequently form the curved portion 21 of the bone contacting outer surface 20 that curves inwards toward the longitudinal axis 5 as it approaches the pointed distal tip 8. A proximal part of the first part 54, and second part 58 of the curved outer surface of the head portion 46 may together subsequently form the neck 18 of the drill bit 10.

The head portion 46 may also include a distal conical portion 56. The distal conical portion 56 may extend distally from the first part 54 of the curved outer surface of the head portion 46. An apex 48 of the distal conical portion 56 may lay on the longitudinal axis 5. Following the formation of the flutes 12A, 12B, 12C, 12D, a remaining part of the distal conical portion 56 (perhaps including the apex 48) may subsequently form the distal pointed tip 8 of the drill bit 10.

To form the flutes 12 of the drill bit 10, a tool such as a cylindrical milling cutter or ball nose cutter may be used to remove material from the head portion 46.

For instance, the use of a cylindrical milling cutter can give rise to flutes 12 that have surfaces that are concave and the shape of a partial cylinder. One cut may be made by the cylindrical milling cutter per flute 12, with each cut being circumferentially spaced around the head portion 46 at positions corresponding to the desired locations of the flutes 12. The cylindrical milling cutter may be oriented at an angle θ with respect to the longitudinal axis 5. Consequently, a cylindrical axis of the concave cylindrical surface of each flute 12 may be oriented at an angle in the range $20°≤θ≤80°$ with respect to the longitudinal axis 5. It is envisaged that a ball nose cutter may instead be used to form flutes 12 that have surfaces that are concave and the shape of a partial cylinder.

As noted previously, it is envisaged that the flutes may have a concave cross-sectional shape other than that of a partial cylinder. For instance, the concave surface may be a V-shaped (with the apex of the "V" pointing inwards, towards the longitudinal axis 5), or square-shaped). These, and other cross sectional shapes for the concave surfaces of the flute may be made using an end mill cutter. An axis of these flutes, analogous to the cylindrical axis noted above, may be oriented at an angle in the range $20°≤θ≤80°$ with respect to the longitudinal axis 5 of the drill bit.

Although in the examples shown in the Figures the path of each flute 12 as it extends proximally from the distal tip 8 is substantially straight, it is also envisaged that the path may be curved. For instance, the path may be substantially helical and/or may curve toward or away from the longitudinal axis 5.

It is also envisaged that each flute 12 may be tilted or angled in one direction to create edges with different angles at either side of the groove formed by each flute 12. This may allow the cutting edges of each flute 12 to have a preferential rotation cutting direction compared to the opposite rotational direction. Moreover, the groove shape or tilt may change across the surface of the head 6, to further vary the edge angle.

FIGS. 5A to 5D show a number of views (cross sections) of the surgical drill bit 10 of the drill bit of FIGS. 1 to 3, each cross section taken in a plane perpendicular to the longitudinal axis 5.

Figure 5A:
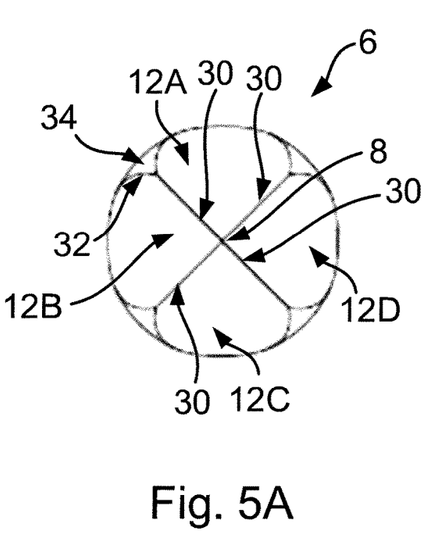
FIG. 5A to 5D show a number of cross sections of the surgical rotational cutting tool of FIGS. 1 to 3, each cross section taken in a plane perpendicular to the longitudinal axis of the tool.

FIG. 5A shows a distal view of the head 6. From FIG. 5A, it can be seen that the drill bit 10 in this example includes four flutes 12A, 12B, 12C, 12D circumferentially positioned at 90° intervals around the head 6. Consequently, the drill bit 10 includes four cutting edges 30, which are also positioned at 90° intervals around the head 6. The V-shaped respective parts 34 of the curved portion 21 of the bone contacting outer surface 20 are also visible in FIG. 5A, showing how these part 34 curve inwards toward the longitudinal axis 5 as they approach the pointed distal tip 8, thereby to make the apexes 36 less prominent.

Figure 5B:
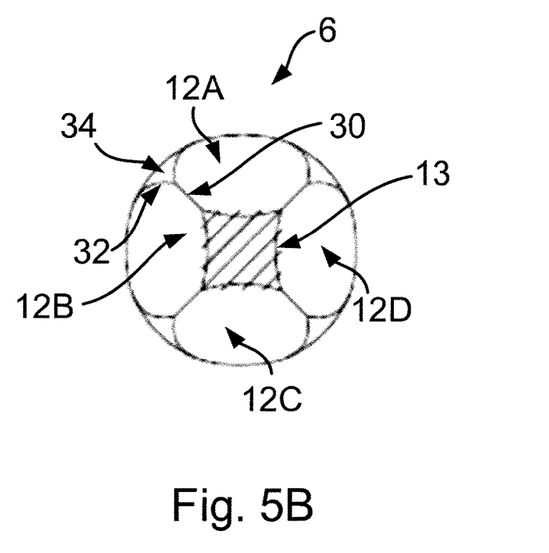

FIG. 5B shows a cross section through the head 6 at a position along the longitudinal axis 5 intermediate the pointed distal tip 8 and the apexes 36. The curved (e.g. substantially cylindrical) shape of the surfaces of the flutes 12A, 12B, 12C, 12D are visible in FIG. 5B.

Figure 5C:
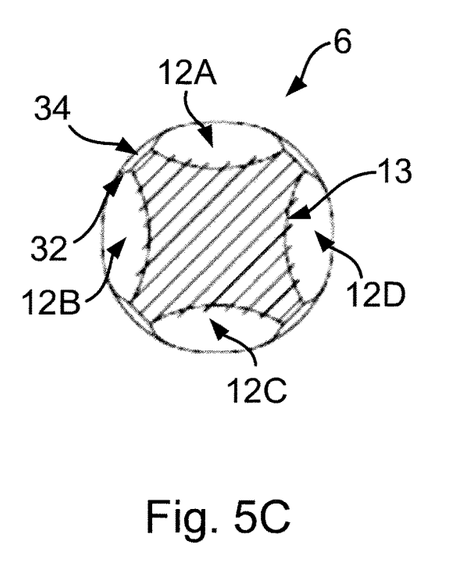

FIG. 5C shows a cross section through the head 6 at a position along the longitudinal axis 5 proximal the apexes 36. The curved (e.g. substantially cylindrical) shape of the surfaces of the flutes 12A, 12B, 12C, 12D is again visible in FIG. 5C.

Figure 5D:
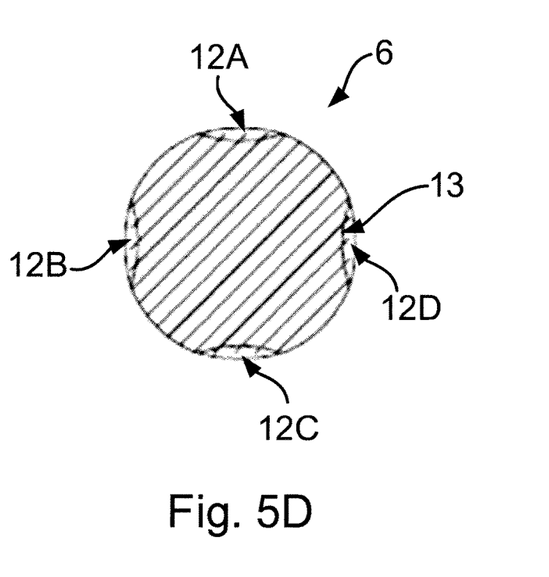

FIG. 5D shows a cross section through the head 6 at a position along the longitudinal axis 5 further proximal the apexes 36 with respect to the cross section of FIG. 5C. The curved (e.g. substantially cylindrical) shape of the surfaces of the flutes 12A, 12B, 12C, 12D is once again visible in FIG. 5C.

In some examples, the drill bit may include a plurality of further cutting edges 38 that are located on the shaft 4 intermediate the head 6 and the proximal end 2. These further cutting edges 38 may be used to make lateral cuts into the bone at a position located proximally with respect to the head 6. An example of the use of a drill bit 10 including further cutting edges 38 will now be described in relation to FIG. 6.

Figure 6:
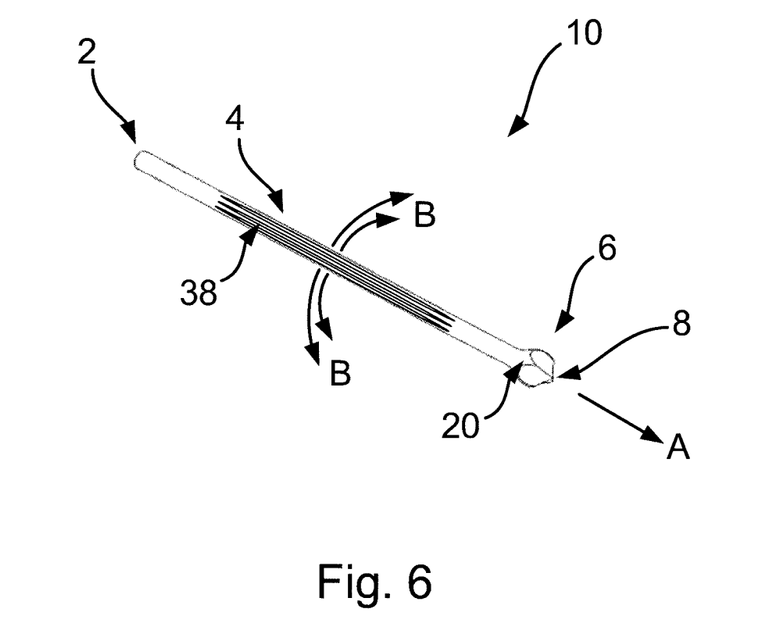
FIG. 6 illustrates the use of a surgical rotational cutting tool of the kind described in FIGS. 1 to 4 in accordance with an embodiment of this invention.

As can be seen in FIG. 6, the drill bit in this example is substantially as described above in relation to FIGS. 1 to 5, with the addition of the plurality of further cutting edges 38. It is envisaged that the drill bit may instead of the kind to be described below in relation to FIGS. 7 to 11 (again, with the addition of the further cutting edges 38 on the shaft 4).

To use the further cutting edges 38, they may be urged laterally against the surface of the bone, as indicated schematically in FIG. 6 by the arrows labelled B. Typically, this may be done after the head 8 has been used to drill into the bone along a direction parallel to the longitudinal axis 5, as indicated in FIG. 6 by the arrow labelled A. In some examples, the further cutting edges 38 may be used to widen an initial opening in the bone made by the head 6. When performing the lateral movements B for urging the further cutting edges 38 laterally against the surface of the bone, it will be appreciated that the head 6 may be located inside the bone.

As described above, the head 6 of the drill bit 10 is configured such that it does not cut laterally into a bone when the drill bit is moved laterally. Where the drill bit 10 includes the further cutting edges 38 for making lateral cuts into the bone at a position located proximally with respect to the head 6, the fact that the head 6 is so configured may allow the further cutting edges 38 with confidence, in the knowledge that this is unlikely to result in unwanted lateral cuts by the head 6.

In one particular example, a surgical rotational cutting tool such as the drill bit 10 may be used to prepare a femur to receive a stem of a femoral prosthetic during a hip replacement procedure. In this example, after cutting away the head and neck of the femur, a drill having a surgical drill bit 10 of the kind described above attached thereto is used to drill through a proximal cut surface of the femur to gain access to the medullary canal. Thereafter, the surgeon may position the drill bit 10 so that the head 6 is located inside the medullary canal, while the further cutting edges 38 are located at the entrance to the medullary canal. The further cutting edges 38 may then be used to remove bone from the medullary canal, by moving the drill bit 10 laterally as described in relation to FIG. 6. This may allow the medullary canal to be shaped to receive the stem. For instance, the further cutting edges 38 may be used to widen the entrance to the medullary canal. In one example, the further cutting edges 38 may be used to remove parts of the piriformis fossa and/or at least part of the greater trochanter that remains after the removal for the femoral neck and head. While the further cutting edges 38 are being used as described above, the head 6 may be located inside the medullary canal. As described above, the configuration of the head 6 may allow the further cutting edges 38 to be used effectively, without causing unwanted lateral removal of bone from the medullary canal by the head 6.

Figure 7:
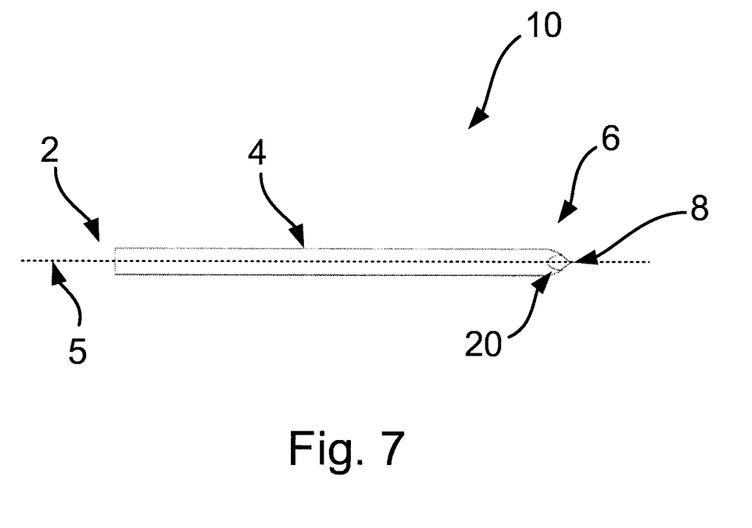
FIGS. 7 and 8 show two views of a surgical rotational cutting tool according to another embodiment of this invention.
Figure 8:
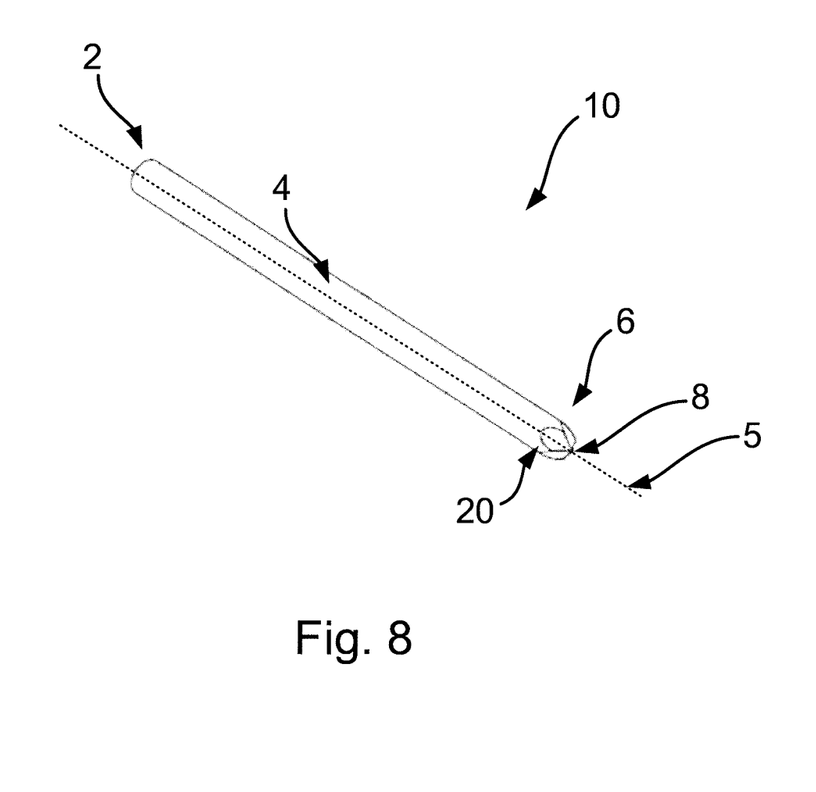
Figure 9:
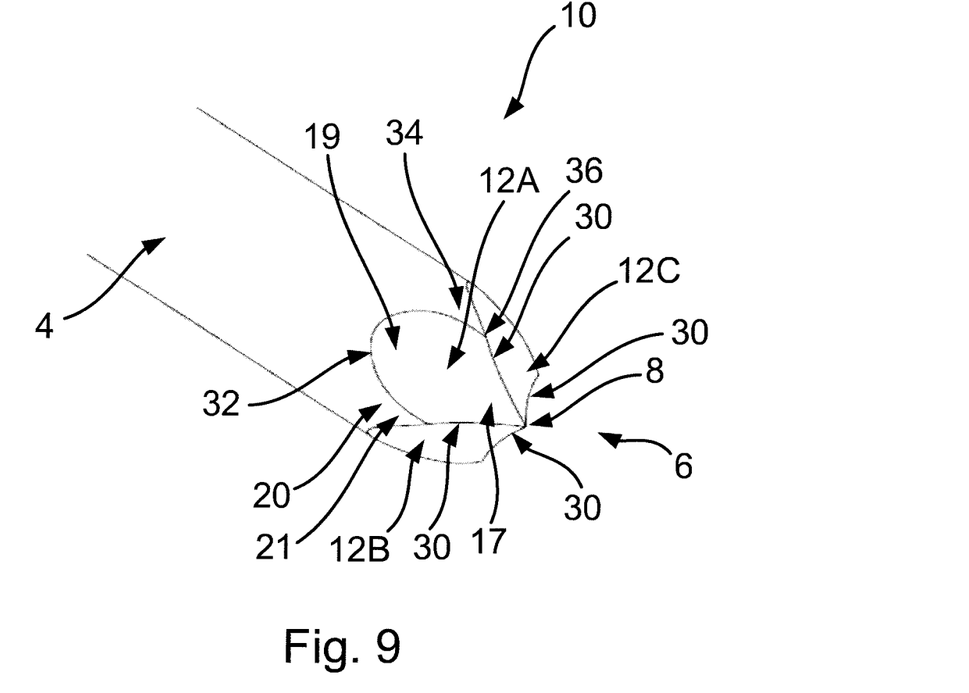
FIG. 9 shows a detailed view of the head of the surgical rotational cutting tool of FIGS. 7 and 8.

FIG. 7 shows a side view of a surgical drill bit 10 for a bone drill according to another embodiment of this invention. An isometric view of the drill bit 10 is shown in FIG. 8. FIG. 9 shows a detailed view of the head 6 of the drill bit 10.

The drill bit in this example is similar to the one described above in relation to FIGS. 1 to 5, with the exception that it does not include a narrowed neck 18 of the kind included in that earlier example. Accordingly, in this example, the bone contacting outer surface 20 does not include a proximal portion that curves inwards toward the longitudinal axis 5 with increasing distance from the pointed distal tip 8 (thereby to form a neck 18 of the kind shown in the embodiment of FIG. 3). Instead, the curved portion 21 of the bone contacting outer surface 20, which curves inwards toward the longitudinal axis 5 as it approaches the pointed distal tip 8, may terminate proximally at the base of the head, where it meets the outer surface of the shaft 4.

In other respects, the configuration of the head 6 in the embodiment of FIGS. 7 to 9 may be similar to that described above in relation to the embodiment of FIGS. 1 to 3.

Figure 10:
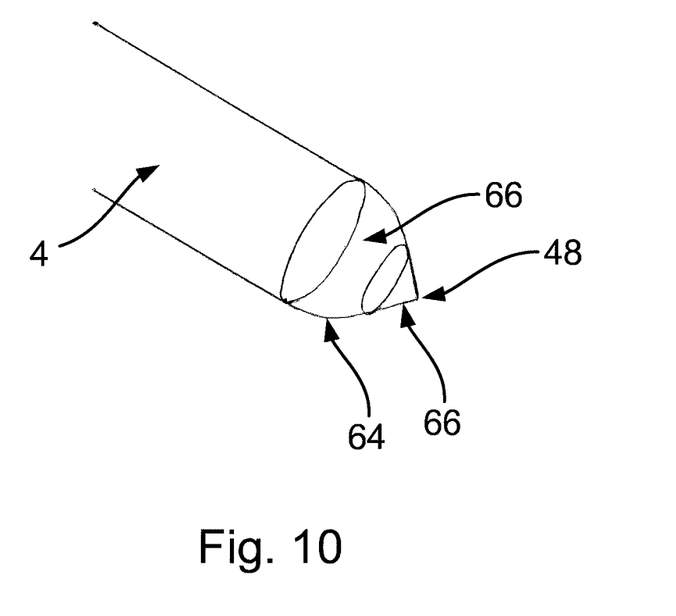
FIG. 10 illustrates a stage in the manufacturing of the surgical rotational cutting tool of FIGS. 7 to 9, prior to the formation of the flutes of the tool.
Figure 11A:
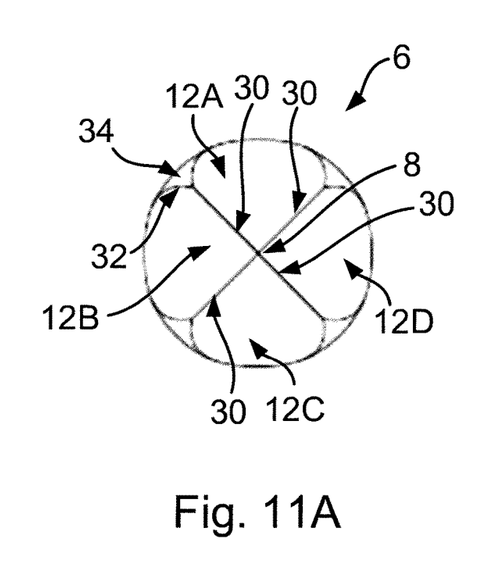
FIGS. 11A to 11D show a number of cross sections of the surgical rotational cutting tool of FIGS. 7 to 9, each cross section taken in a plane perpendicular to the longitudinal axis of the tool.
Figure 11B:
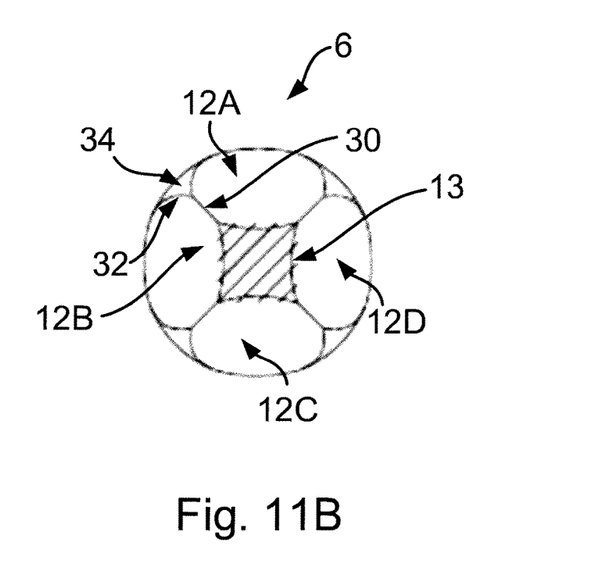
Figure 11C:
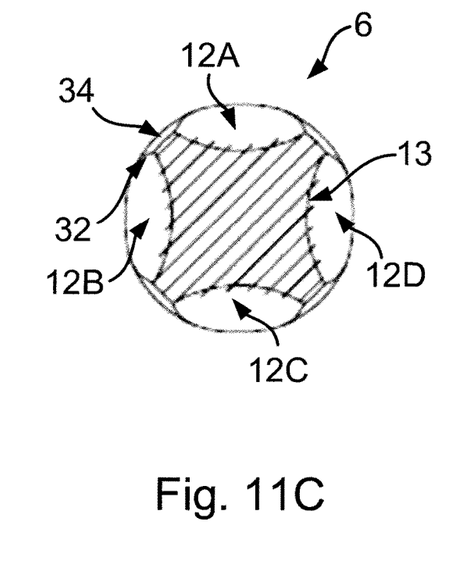
Figure 11D:
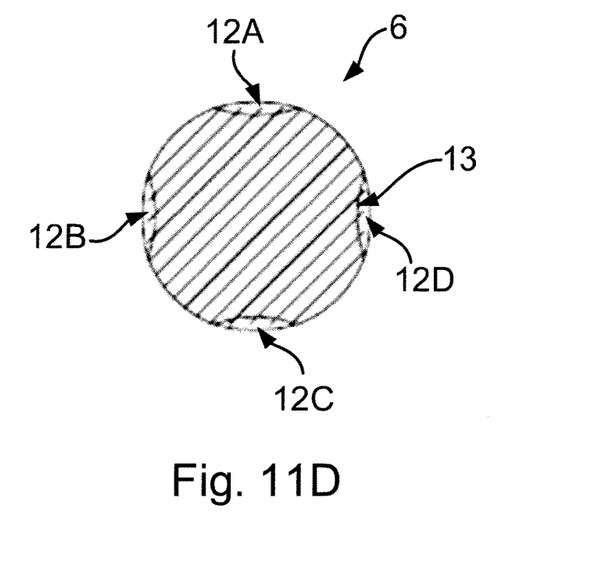

FIG. 10 illustrates a stage in the manufacturing of the surgical drill bit of FIGS. 7 to 9, prior to the formation of the flutes 12A, 12B, 12C, 12D. Again, it is envisaged that the same or a similar approach may be used for manufacturing other surgical rotational cutting tools such as rotary initiator devices (also known as a canal initiator tips), or straight reamers.

To form the drill bit 10, there may first be provided a work piece that comprises the shaft 4 of the drill bit 10, with a head portion 66. In the present example, the head portion 66 has a curved outer surface 64, the remaining parts of which (i.e. following the formation of the flutes 12A, 12B, 12C, 12D) will subsequently form the curved portion 21 of the bone contacting outer surface 20 of the drill bit 10. The curved outer surface 64 may be substantially spherical (i.e. it may correspond in shape to a portion of the surface of a sphere).

The head portion 66 may also include a distal conical portion 66. The distal conical portion 66 may extend distally from the curved outer surface 64. An apex 48 of the distal conical portion 66 may lay on the longitudinal axis 5. Following the formation of the flutes 12A, 12B, 12C, 12D, a remaining part of the distal conical portion 66 (perhaps including the apex 48) may subsequently form the distal pointed tip 8 of the drill bit 10.

Starting with the work piece shown in FIG. 10, a cylindrical milling cutter or a ball nose cutter may be used substantially as described above in relation to FIG. 4 to form the flutes 12, resulting in a drill bit 10 of the kind shown in FIGS. 7 to 9. Again, in embodiments in which the flutes 12 are V-shaped or square, then an end mill cutter may be used to form the flutes 12 instead.

FIG. 11A to 11D show a number of views (cross sections) of the surgical drill bit 10 of the drill bit of FIGS. 7 to 9, each cross section taken in a plane perpendicular to the longitudinal axis 5. The views (cross sections) in FIGS. 11A to 11D are at the same positions along the longitudinal axis 5 as those in FIGS. 5A to 5D. Comparison of the views in FIGS. 5A to 5D with those in FIGS. 11A to 11D demonstrate that the head 6 of the drill bit 10 of this second embodiment is similarly configured to the head 6 in the first embodiment, at least in positions distal the proximal end of the curved portion 21.

The surgical rotational cutting tools described herein may comprise a material such as stainless steel. By way of example, 400 or 600 series stainless steel cold be used (e.g. 17/4 PH (600 series); 420 S29/S45; 440 B, or 440C).

Embodiments of this invention can allow the functions of a pointed tip for initially drilling into a bone, and a lateral reamer, to be combined in a single tool. This can save manufacturing costs in the production surgical instruments for performing a surgical procedure, and can reduce the weight and size of a surgical kit incorporating the drill bit.

According to embodiments of this invention, a surgical kit may be provided. The kit may, for instance be a kit for a hip replacement procedure. The kit may include a plurality of surgical rotational cutting tools (e.g. drill bits) of the kind set out above. It is envisaged that some of the surgical rotational cutting tools may be of different sizes.

Accordingly, there has been described a surgical rotational cutting tool, a surgical kit and a method of preparing a femur to receive a stem of a femoral prosthetic. The tool includes a longitudinal axis and a shaft extending along the longitudinal axis, which has a proximal end and a distal end. The tool also includes a head located at the distal end of the shaft. The head includes a pointed distal tip, a bone contacting outer surface having a portion which curves inwards toward the longitudinal axis as it approaches the tip, and a plurality of flutes. The edges of distal parts of neighbouring pairs of the flutes meet to define a plurality of cutting edges which extend proximally from the pointed distal tip. A proximal part of each flute extends proximally across the curved portion.

Although particular embodiments of the invention have been described, it will be appreciated that many modifications/additions and/or substitutions may be made within the scope of the claimed invention.

The invention claimed is:

1. A surgical rotational cutting tool comprising:
   a longitudinal axis;
   a shaft extending along the longitudinal axis and having a proximal end and a distal end; and
   a head located at the distal end of the shaft, the head comprising:
      a pointed distal tip;
      a bone contacting outer surface having a curved portion which curves inwards toward the longitudinal axis as it approaches the tip; and
      a plurality of flutes positioned circumferentially around the head, wherein each flute includes a proximal part and a distal part, wherein each distal part extends proximally from the pointed distal tip, wherein edges of the distal parts of neighboring pairs of said circumferentially positioned flutes meet to define a plurality of cutting edges which extend proximally from the pointed distal tip, and wherein the proximal part of each flute extends proximally across the curved portion of the bone contacting outer surface; wherein an angle(s) at which the edges of the distal parts of said neighboring pairs of flutes meet to define the plurality of cutting edges are more acute than an angle(s) at the edges formed between the proximal part of each flute and the bone contacting outer surface.

2. The surgical rotational cutting tool of claim 1 comprising a plurality of further cutting edges located on the shaft intermediate the head and the proximal end of the shaft.

3. The surgical rotational cutting tool of claim 1, wherein the cutting edges extending proximally from the pointed distal tip are concave.

4. The surgical rotational cutting tool of claim 1, wherein each flute comprises a concave surface.

5. The surgical rotational cutting tool of claim 4, wherein an axis of the concave surface of each flute is oriented at an angle in the range 20°≤θ≤80° with respect to the longitudinal axis.

6. The surgical rotational cutting tool of claim 4, wherein the concave surface of each flute is a concave cylindrical surface.

7. The surgical rotational cutting tool of claim 1, wherein the proximal parts of respective neighboring pairs of flutes are separated from each other by a respective part of the curved portion of the bone contacting outer surface.

8. The surgical rotational cutting tool of claim 7, wherein each respective part of the curved portion of the bone contacting outer surface is substantially V-shaped, and wherein the apex of each substantially V-shaped part meets a proximal end of the cutting edge that is defined by said respective neighboring pair of flutes.

9. The surgical rotational cutting tool of claim 1, wherein the bone contacting outer surface has a proximal portion that curves inwards toward the longitudinal axis with increasing distance from the pointed distal tip, to form a neck of the surgical rotational cutting tool.

10. The surgical rotational cutting tool of claim 9, wherein the proximal part of each flute extends proximally across the proximal portion of the bone contacting outer surface.

11. The surgical rotational cutting tool of claim 1, wherein at least part of the bone contacting outer surface is substantially spherical.

12. The surgical rotational cutting tool of claim 1 wherein the flutes are equally circumferentially spaced around the head.

13. The surgical rotational cutting tool of claim 1 comprising four of said flutes.

14. The surgical rotational cutting tool of claim 1, wherein the tool is a surgical drill bit, rotary initiator device, or a straight reamer.

15. A surgical rotational cutting tool comprising:
a longitudinal axis;
a shaft extending along the longitudinal axis and having a proximal end and a distal end; and
a head located at the distal end of the shaft, the head comprising:
  a pointed distal tip;
  a bone contacting outer surface having a curved portion which curves inwards toward the longitudinal axis as it approaches the tip; and
  a plurality of flutes positioned circumferentially around the head, wherein each flute includes a proximal part and a distal part, wherein each distal part extends proximally from the pointed distal tip, wherein edges of the distal parts of neighboring pairs of said circumferentially positioned flutes meet to define a plurality of cutting edges which extend proximally from the pointed distal tip, and wherein the proximal part of each flute extends proximally across the curved portion of the bone contacting outer surface; wherein the cutting edges extending proximally from the pointed distal tip are concave.

16. A surgical rotational cutting tool comprising:
a longitudinal axis;
a shaft extending along the longitudinal axis and having a proximal end and a distal end; and
a head located at the distal end of the shaft, the head comprising:
  a pointed distal tip;
  a bone contacting outer surface having a curved portion which curves inwards toward the longitudinal axis as it approaches the tip; and
  a plurality of flutes positioned circumferentially around the head, wherein each flute includes a proximal part and a distal part, wherein each distal part extends proximally from the pointed distal tip, wherein edges of the distal parts of neighboring pairs of said circumferentially positioned flutes meet to define a plurality of cutting edges which extend proximally from the pointed distal tip, and wherein the proximal part of each flute extends proximally across the curved portion of the bone contacting outer surface; wherein each flute comprises a concave surface.

* * * * *